United States Patent
Hitce

(10) Patent No.: US 10,144,690 B2
(45) Date of Patent: Dec. 4, 2018

(54) 1,2-DIPHENYLETHYLENE GLYCOL COMPOUNDS FOR COMBATING AGING OF THE SKIN, AND COSMETIC USE THEREOF

(71) Applicant: L'OREAL, Paris (FR)

(72) Inventor: Julien Hitce, Aulnay-sous-Bois (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 15/534,174

(22) PCT Filed: Dec. 11, 2015

(86) PCT No.: PCT/EP2015/079429
§ 371 (c)(1),
(2) Date: Jun. 8, 2017

(87) PCT Pub. No.: WO2016/092076
PCT Pub. Date: Jun. 16, 2016

(65) Prior Publication Data
US 2017/0362152 A1    Dec. 21, 2017

(30) Foreign Application Priority Data
Dec. 12, 2014   (FR) ...................... 14 62361

(51) Int. Cl.
| A61K 8/34 | (2006.01) |
| A61Q 19/08 | (2006.01) |
| C07C 39/15 | (2006.01) |
| C07C 43/23 | (2006.01) |

(52) U.S. Cl.
CPC .............. *C07C 43/23* (2013.01); *A61K 8/345* (2013.01); *A61K 8/347* (2013.01); *A61Q 19/08* (2013.01); *C07C 39/15* (2013.01)

(58) Field of Classification Search
CPC ........ A61K 8/345; A61K 8/347; A61Q 19/08; C07C 39/15; C07C 43/23
See application file for complete search history.

(56) References Cited

U.S. PATENT DOCUMENTS 8,921,614 B1 * 12/2014 Davis .................... C07C 303/28
568/729
2004/0122083 A1 * 6/2004 Pettit .................... C07D 317/22
514/463

FOREIGN PATENT DOCUMENTS

| EP | 2 674 155 A1 | 12/2013 |
| FR | 2 900 046 A1 | 10/2007 |
| WO | WO-2012/131072 A1 | 10/2012 |

OTHER PUBLICATIONS

Schaaf et al., Chemische Konstitution und Wirkung im Akanthosetest, Dermatologica, 123:362-374 (1961).
Ali et al., "Phenolic Constituents of *Gnetum klossii*", J. Nat. Prod., 2003, 66, 556-560.
Porcu et al., "The emerging therapeutic potential of sirtuin-interacting drugs: from cell death to lifespan extension", Trends in Pharmacological Sciences, Col. 26, No. 2, Feb. 2005, 94-103.
Xiao et al., "Constituents from *Polygonum cuspidatum*", Chem. Pharm. Bull., 50(5) 605-608 (2002).
Woo et al., "DNA Topoisomerases I and II Inhibitory Activity and Cytotoxicity of Compounds from the Stems of *Parthenocissus tricuspidata*", DNA Topoisomerases Inhibition and Cytotoxicity Parthenocissus tricuspidata Bull. Korean Chem Soc., 2013, vol. 34, No. 9, 2675-2679.

* cited by examiner

Primary Examiner — Alma Pipic
(74) Attorney, Agent, or Firm — Polsinelli PC

(57) ABSTRACT

The present invention relates to novel compounds of formula (I)

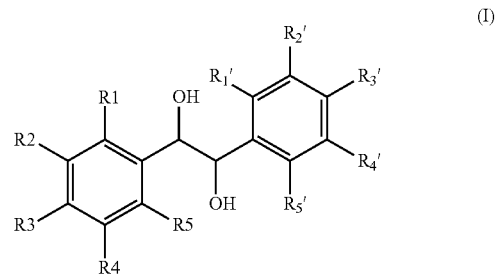

to cosmetic compositions comprising same, and also to the use thereof for preventing and/or cosmetically treating the signs of aging of the skin.

21 Claims, No Drawings

1,2-DIPHENYLETHYLENE GLYCOL COMPOUNDS FOR COMBATING AGING OF THE SKIN, AND COSMETIC USE THEREOF

CROSS REFERENCE TO RELATED APPLICATIONS

This application is a National Phase filing under 35 U.S.C. § 371 of PCT/EP2015/079429 filed on Dec. 11, 2015; and this application claims priority to Application No. 1462361 filed in France on Dec. 12, 2014 under 35 U.S.C. § 119. The entire contents of each application are hereby incorporated by reference.

The present invention relates to the use of 1,2-diphenylethylene glycol derivatives for combating aging of the skin and also relates to novel 1,2-diphenylethylene glycol compounds, and to compositions, especially cosmetic compositions, comprising them.

Women and men currently have a tendency to wish to appear youthful for as long as possible and consequently seek to tone down the signs of aging of the skin, which are reflected especially by wrinkles and fine lines. In this regard, the advertising and fashion industries mention products for retaining radiant and wrinkle-free skin, which are signs of youthful skin, for as long as possible, all the more so since physical appearance has an effect on the psyche and/or on morale.

Hitherto, wrinkles and fine lines were treated using cosmetic products containing active agents acting on the skin, for example by improving its cell renewal or alternatively by promoting the synthesis, or preventing the degradation, of the elastic fibers which make up skin tissue.

The skin consists of two compartments, a surface compartment, the epidermis, and the other deeper compartment, the dermis, which interact. Natural human epidermis is composed mainly of three types of cells, namely keratinocytes, which form the vast majority, melanocytes and Langerhans cells. Each of these types of cells contributes, by virtue of its intrinsic functions, to the essential role played in the body by the skin, especially the role of protecting the body against external attacking factors, which is known as the "barrier function".

The epidermis is conventionally divided into a basal layer of keratinocytes that constitutes the germinative layer of the epidermis, a spinous layer consisting of several layers of polyhedral cells positioned on the germinative layers, one to three "granular" layers consisting of flattened cells containing distinct cytoplasmic inclusions, keratohyalin granules, and finally the cornified layer (or stratum corneum), consisting of a set of layers of keratinocytes at the terminal stage of their differentiation, known as corneocytes. Corneocytes are anuclear cells mainly consisting of a fibrous material containing cytokeratins, surrounded by a cornified envelope.

The dermis provides the epidermis with a solid support. It is also its nourishing element. It consists mainly of fibroblasts and of an extracellular matrix predominantly composed of collagen, elastin and a substance, known as ground substance, comprising glycosaminoglycans that are sulfated (e.g. chondroitin sulfate) or not (e.g. hyaluronic acid), proteoglycans and various proteases. These components are synthesized by the fibroblasts. Leukocytes, mast cells or else tissue macrophages are also found therein. Finally, blood vessels and nerve fibers pass through the dermis. The cohesion between the epidermis and the dermis is provided by the dermo-epidermal junction.

The epidermis is constantly engaged in producing new keratinocytes to compensate for the continuous loss of epidermal cells at the cornified layer. However, in the course of aging, a decrease in the number of cells in the proliferation phase, and consequently a decrease of the live epidermal layers, may be observed physiologically.

The homeostasis of the skin, and in particular of the epidermis, results from a finely regulated balance between the processes of proliferation and of differentiation of the skin cells. These processes of proliferation and differentiation are entirely regulated: they participate in the renewal and/or regeneration of the skin and lead to the maintenance of a constant thickness of the skin, and in particular of a constant thickness of the epidermis. This homeostasis of the skin also participates in maintaining the mechanical properties of the skin.

However, this homeostasis of the skin may be impaired by certain physiological factors (age, menopause, hormones, etc.) or environmental factors (UV stress, oxidative stress, irritant stress, etc.).

The proliferative cells are metabolically very active and are sensitive to these deleterious factors (intrinsic or environmental), with, as a consequence on the epidermis, a reduction in their amount. Certain biochemical markers characterize this loss of regenerative capacity of the epidermis such as the Sab galactosidase activity (Dimri G P, et al. Proc Natl Acad Sci USA. 1995) or markers of impairment of the cell cycle such as p16(INK4a) (Cordisco S et al., J Invest Dermatol. 2010).

It is thus important to preserve this pool of cells in order to contribute toward delaying the onset of the signs of aging.

The cellular vitality of the keratinocytes may be decreased especially in the context of aging or on account of oxidative stress (for example solar radiation, i.e. UV, visible light, infrared), on account of attack of the epidermis by toxins or metabolites of the microflora, or, more generally, during chronological aging. The capacity for renewal and differentiation of the keratinocytes is reduced and the homeostasis of structures dependent thereon, such as the barrier function of the epidermis, is impaired.

When the regenerative potential of the epidermis becomes smaller: the cells of the basal layer divide less actively, leading especially to a slowing-down and/or decrease in epidermal renewal. Consequently, the cell renewal no longer compensates for the loss of cells removed at the surface, leading to atrophy of the epidermis and/or a reduction in skin thickness. This is likewise the case for the proliferative cells of the epidermal appendages, for example the nails, the consequence of which is a slowing-down of the growth of the nails.

Impairments in epidermal homeostasis are also reflected by a dull and/or off-color appearance of the skin complexion.

Impairment of the barrier function is manifested by various signs depending on the localization: dry skin, hyperkeratosis, thin epidermis, thin lips, surface wrinkles.

The disorders associated with impairment of the cellular vitality of the epidermis thus concern not only its structure, but also its homeostasis. The resistance to stress of the epidermis and its capacity for regeneration are reduced. If the skin barrier of an elderly person is compared with that of a young adult, the differences do not appear at first sight: the thickness of the cornified layer and the composition of its lipids are not necessarily altered, and the barrier function expressed by the transepidermal water loss is conserved. The deficiencies of the elderly skin barrier appear under mechanical stress or during exposure to irritant factors: the barrier of an elderly epidermis degrades more rapidly and its function recovers less quickly. On a daily basis, alcoholic disinfection, contact with lemon juice or other irritants then cause stinging and burning, and dry air is poorly tolerated, whereas a young skin tolerates this without any problem. An impaired skin barrier also facilitates the contact of allergens with the immune system of the epidermis, thus increasing the risk of allergic sensitization.

At the present time, there is sufficient evidence to prove that senescent cells accumulate with age in the body. Senescence-associated β-galactosidase is a marker of senescent cells and its accumulation has been shown in vivo in the skin (Dimai G P et al Proc Nat Acad. Sci. USA. 1995; 92(20): 9363-7).

Another marker of senescence is the impairment of mitochondrial functioning. The role of the mitochondrion is to produce cellular energy.

The clinical signs of the phenomenon of photoaging have been widely described (Photodermatol Photoimmunol Photomed. 2008 (4) Fourtanier A., Moyal D., Seité S.).

Intrinsic aging, also known as chronological aging, of the skin is described as a result of an impairment in cellular vitality similar to that which takes place in the other organs. Intrinsic or chronological aging is manifested by other clinical markers and signs, in particular impairment of the barrier function as described above (Farage M. A. et al. 2009; 10(2): 73-86).

These esthetic disorders such as dry skin, wrinkles, fine lines, etc. are such that there is a need in cosmetics for compounds acting on the skin to improve the cellular vitality when it is impaired.

AMPK is present in all the cells of the body and plays an energy gauge role therein. AMPK (or 5'-adenosine monophosphate activated protein kinase) is a heterotrimeric enzyme composed of a catalytic subunit a with kinase activity and two regulatory subunits βand γ. The activity of AMPK depends on the variation of the AMP/ATP ratio which characterizes the energy level of the cell (ATP being hydrolyzed into AMP to "deliver" the energy required for the various biochemical processes of the cell). It is present in two forms, phosphorylated or non-phosphorylated, the phosphorylated form being the active form.

When it is activated in response to an energy demand or a stress of the cell, AMPK increases the energy-generating processes such as glycolysis and it inhibits the non-essential consuming processes, thus enabling cell survival. Preservation of the cellular energy status is involved in maintaining the longevity of the species and combating the signs of aging. Thus, compounds that are capable of increasing the activity of AMPK are at the present time the object of great interest in the treatment of age-related clinical manifestations. The value in transposing this approach, validated for the whole organism, to the skin in the context of preventing its age-related impairment may be understood.

The AMPK activity corresponds to the cellular concentration of phosphorylated AMPK. Thus, it is worthwhile having the highest possible levels of phosphorylated protein in order to have this high activity.

The role of AMPK in controlling the energy metabolism of the keratinocyte is suspected at the present time (Prahl S et al., Biofactors. 2008; 32(1-4): 245-55), its involvement in the proliferation and differentiation of the keratinocyte has been established (Saha A. K. et al. Biochem. Biophys. Res. Commun. 2006 Oct. 20; 349(2): 519-24).

WO 2004/05098 proposes to modulate the lifetime of any cell or of an organism by controlling the activity of AMPK, and to treat age-related disorders by administering modulators of the AMPK metabolic pathway, without stating whether it involves an activator or an inhibitor.

Saha et al. (Biochem. Biophys. Res. Commun 2006, 349:519-524) studied the AMPK-regulated growth of keratinocytes and conclude that AMPK activators such as AICAR promote the in vitro differentiation of keratinocytes.

It has been found, unexpectedly, in the context of the present invention, that certain 1,2-diphenylethylene glycol derivatives described below are capable of stimulating the activity of AMPK, in particular the production of phosphorylated AMPK by normal human keratinocytes. These compounds will thus be particularly useful for combating the decrease in the vitality of skin cells during aging, and retarding the onset of the signs associated therewith.

The use according to the invention is a non-therapeutic use and advantageously a cosmetic use; the term "cosmetic" means intended to improve the esthetic appearance of the skin or its appendages such as the nails, especially to retard or reduce physiological modifications in the appearance, arising with age, of individuals in good health. These modifications may appear from the age of 30 or 35, but are generally more pronounced after the age of 40, and become accentuated at 50 and over.

The compounds according to the invention are effective for improving epidermal renewal and for more efficiently combating the signs of aging of the skin.

These compounds therefore find a particular application in cosmetic compositions intended for preventing and/or cosmetically treating aging of the skin; especially preventing and/or treating, in particular topically, the signs of aging of the skin, and most particularly the signs on the skin related to wrinkled skin, skin exhibiting impairment of its viscoelastic or biomechanical properties, skin exhibiting impairment in the cohesion of its tissues, thinned skin and/or skin exhibiting impairment of its surface appearance.

Specifically, it has now been found that 1,2-diphenylethylene glycol derivatives are capable of stimulating the activation of AMPK by the keratinocytes.

As explained above, the activation of AMPK, in particular the increase of its phosphorylated form, corresponds to stimulation of the metabolic functions of keratinocytes: these cells are then in a state similar to those of young keratinocytes, and will contribute toward regulating the physiological mechanisms of cutaneous homeostasis.

The use of the compounds according to the invention may make it possible more particularly to maintain and/or restore the biomechanical properties of the skin.

The term "biomechanical properties of the skin" means herein the stretchability, tonicity, firmness, suppleness and/or elasticity properties of the skin.

The term "signs of aging of the skin" means herein any modification of the outer appearance of the skin due to aging, whether it is chronobiological and/or extrinsic aging, in particular photoinduced or hormonal aging; among these signs, it is possible to distinguish:
  wrinkled skin, which is reflected especially by the appearance of wrinkles and/or fine lines;
  skin exhibiting impairment of its viscoelastic or biomechanical properties, or skin exhibiting a lack of elasticity and/or of stretchability and/or of firmness and/or of suppleness and/or of tonicity, which is reflected in particular by wizened, flaccid, slack or saggy skin;
  skin exhibiting impairment of the cohesion of its tissues; thinned skin; and
  skin exhibiting impairment of its surface appearance, which is especially reflected by impairment of the grain of the skin, for example roughness.

The invention relates to the non-therapeutic use of one or more compounds of formula (I) according to the invention, as agents for preventing and/or reducing the signs of aging of the skin, especially the signs on the skin chosen from wrinkled skin, skin exhibiting impairment of its viscoelastic or biomechanical properties, skin exhibiting impairment in the cohesion of its tissues, thinned skin, and skin exhibiting impairment of its surface appearance.

Particularly the invention relates to the non-therapeutic use of one or more compounds of formula (I) according to the invention in which R3' denotes a radical —OR, R denotes a hydrogen atom or a linear C1-C6 or branched C3-C6 alkyl or linear C1-6 acyl radical, as agents for preventing and/or reducing the signs of aging of the skin, especially the signs on the skin chosen from wrinkled skin, skin exhibiting impairment of its viscoelastic or biomechanical properties, skin exhibiting impairment in the cohesion of its tissues, thinned skin, and skin exhibiting impairment of its surface appearance.

Preferably the skin of individuals which are humans.

The invention also relates to a composition, especially a cosmetic composition, comprising, in a physiologically acceptable medium, at least one compound of formula (I) according to the invention.

The invention also relates to the use of a composition, especially a cosmetic composition, comprising, in a physiologically acceptable medium, at least one compound of formula (I).

The invention also relates to a non-therapeutic cosmetic process for treating the skin, comprising the application to the skin of at least one compound of formula (I) and/or of a cosmetic composition containing at least one compound of formula (I) according to the invention. This process finds an advantageous application in the treatment of the skin, especially of mature skin (skin of individuals with age at least 40) and/or wrinkled skin, in particular of the face, especially of the forehead, the neck, the neckline and/or the hands. A subject of the invention is also a cosmetic treatment process, characterized in that it is intended for promoting the renewal of the keratinocytes and for reducing or preventing signs chosen from thinning of the epidermis, surface wrinkles and impairment of the barrier function.

Particularly the invention relates to a non-therapeutic cosmetic process for treating the skin, comprising the application to the skin of at least one compound of formula (I) and/or of a cosmetic composition containing at least one compound of formula (I) according to the invention, said compound of formula (I) is compound in which in which R3' denotes a radical —OR, R denotes a hydrogen atom or a linear C1-C6 or branched C3-C6 alkyl or linear C1-6 acyl radical. This process finds an advantageous application in the treatment of the skin, especially of mature skin and/or wrinkled skin, in particular of the face, especially of the forehead, the neck, the neckline and/or the hands. A subject of the invention is also a cosmetic treatment process, characterized in that it is intended for promoting the renewal of the keratinocytes and for reducing or preventing signs chosen from thinning of the epidermis, surface wrinkles and impairment of the barrier function.

A subject of the present invention is also novel 1,2-diphenylethylene glycol compounds of formula (IIIA) as defined below.

A subject of the present invention is also compositions, especially cosmetic compositions, comprising, in a physiologically acceptable medium, at least one compound of formula (IIIA).

Particularly a subject of the present invention is also compositions, especially cosmetic compositions, comprising, in a physiologically acceptable medium, at least one compound of formula (IIIA), with the exception of compound 9 as defined below.

The invention also relates to the non-therapeutic use of the novel compounds of formula (IIIA) or of a composition, especially a cosmetic composition, of a novel compound of formula (IIIA), in particular as an agent for preventing and/or reducing the signs of aging of the skin, especially the signs on the skin chosen from wrinkled skin, skin exhibiting impairment of its viscoelastic or biomechanical properties, skin exhibiting impairment in the cohesion of its tissues, thinned skin, and skin exhibiting impairment of its surface appearance.

The invention finally relates to a non-therapeutic cosmetic process for treating the skin, comprising the application to the skin of at least one novel compound of formula (IIIA) and/or of a cosmetic composition containing at least one novel compound of formula (IIIA) according to the invention. This process finds an advantageous application in the treatment of the skin, especially of mature skin and/or wrinkled skin, in particular of the face, especially of the forehead, the neck and/or the hands.

Particularly the invention relates to use of one or more compounds of formula (I):

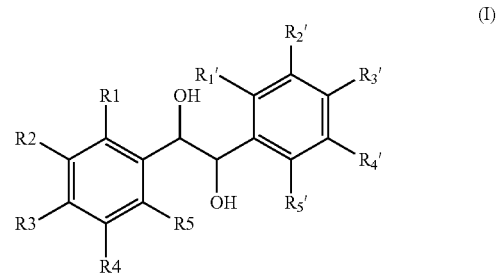

(I)

in which R1, $R_1'$, R2, $R_2'$, R3, R4, $R_4'$, R5 and $R_5'$ independently denote a hydrogen atom or a radical —OR, and $R_3'$ denotes a radical —OR, R denotes a hydrogen atom, a linear C1-C6 alkyl, a branched C3-C6 alkyl, or a linear C1-C6 acyl radical, and also an optical isomer, stereoisomer and/or diastereoisomer and/or salts thereof, as an agent for preventing and/or reducing the signs of aging of the skin, especially the signs on the skin chosen from wrinkled skin, skin exhibiting impairment of its viscoelastic or biomechanical properties, skin exhibiting impairment in the cohesion of its tissues, thinned skin, and skin exhibiting impairment of its surface appearance.

The compounds according to the invention thus correspond to formula (I) below:

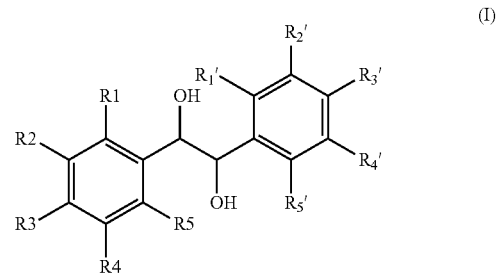

(I)

in which R1, $R_1'$, R2, $R_2'$, R3, $R_3'$, R4, $R_4'$, R5 and $R_5'$ independently denote a hydrogen atom or a radical —OR, R denoting a hydrogen atom, a linear C1-C6 alkyl, branched C3-C6 alkyl, or a linear C1-C6 acyl radical, and also an optical isomer, stereoisomer and/or diastereoisomer and/or salts thereof.

Preferentially, the linear saturated or branched alkyl groups may be chosen from methyl, ethyl, propyl, isopropyl, butyl, isobutyl and tert-butyl, more preferentially methyl.

Preferably:

R1, $R_1'$, R2, $R_2'$, R3, R4, $R_4'$, R5 and $R_5'$ independently denote a hydrogen atom or a radical —OR, and $R_3'$ denotes a radical —OR, R denotes a hydrogen atom, a linear C1-C6 alkyl, a branched C3-C6 alkyl, or a linear C1-C6 acyl radical, Preferably:

R1, $R_1'$, R5 and $R_5'$, denote a hydrogen atom,

R2, $R_2'$, R3, R4 and $R_4'$ independently denote a hydrogen atom or a radical —OT1 in which T1 denotes a hydrogen atom or a linear C1-C4 alkyl radical; preferably, T1 denotes a hydrogen atom or a methyl radical, and $R_3'$, denotes or a radical —OT1 in which T1 denotes a hydrogen atom or a linear C1-C4 alkyl radical; preferably, T1 denotes a hydrogen atom or a methyl radical.

In a first preferred variant of the invention, among the compounds of formula (I), or an optical isomer, stereoisomer and/or diastereoisomer and/or salts thereof, the compounds that will be chosen are those for which

R1=$R_1'$,
R2=$R_2'$,
R3=$R_3'$,
R4=$R_4'$,
R5=$R_5'$ i.e. the compounds corresponding to formula (II) below:

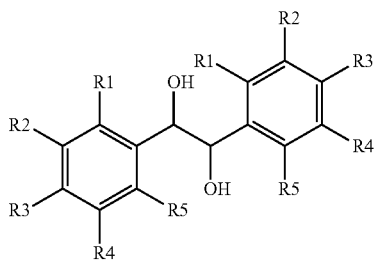

(II)

in which R1, R2, R3, R4 and R5 independently denote a hydrogen atom or a radical —OR, R denotes a hydrogen atom, a linear C1-C6 alkyl, a branched C3-C6 alkyl, or a linear C1-C6 acyl radical.

Preferably:

R1, R2, R4 and R5 independently denote a hydrogen atom or a radical —OR, R denotes a hydrogen atom, a linear C1-C6 alkyl, a branched C3-C6 alkyl, or a linear C1-C6 acyl radical, and R3 denotes a radical —OR, R denotes a hydrogen atom, a linear C1-C6 alkyl, a branched C3-C6 alkyl, or a linear C1-C6 acyl radical.

Preferably:

R1 and R5 denote a hydrogen atom

R2, R3 and R4 independently denote a hydrogen atom or a radical —OT2 in which

T2 denotes a hydrogen atom or a linear C1-C4 alkyl radical.

More particularly, T2 denotes a hydrogen atom or a methyl radical.

Preferably:

R1 and R5 denote a hydrogen atom

R2 and R4 independently denote a hydrogen atom or a radical —OT2 in which T2 denotes a hydrogen atom or a linear C1-C4 alkyl radical, more particularly, T2 denotes a hydrogen atom or a methyl radical, and R3 denotes a radical —OT2 in which T2 denotes a hydrogen atom or a linear C1-C4 alkyl radical, more particularly, T2 denotes a hydrogen atom or a methyl radical.

Among the compounds of formula (II), compounds 1 to 3 below, the optical isomers, stereoisomers and diastereoisomers thereof or geometrical isomers thereof or salts thereof or salts thereof will be chosen more particularly:

| Compound | Structure |
|---|---|
| 1 | 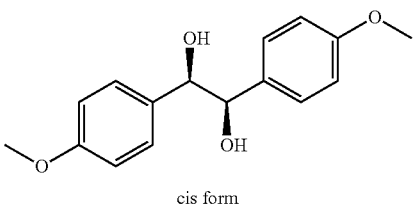<br>cis form |
| 2 | 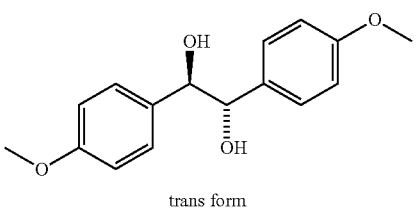<br>trans form |
| 3 | 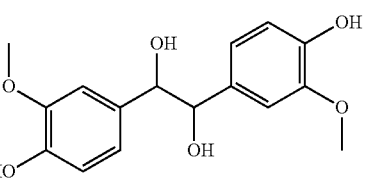 |

In a second preferred variant of the invention, among the compounds of formula (I), or an optical isomer, stereoisomer and/or diastereoisomer and/or salts thereof, the compounds for which R1=R3=R5=hydrogen, i.e. the compounds corresponding to formula (III) below, will be chosen:

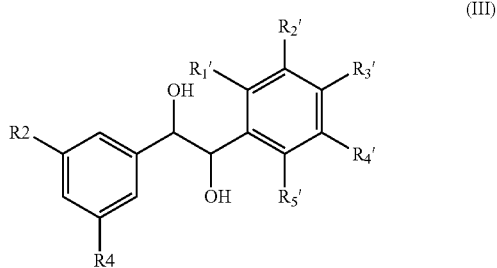

(III)

in which:

R2 and R4 independently denote a radical —OR $R_1'$, $R_2'$, $R_3'$, $R_4'$ and $R_5'$ independently denote a hydrogen atom or a radical —OR R denotes a hydrogen atom, a linear C1-C6 alkyl, a branched C3-C6 alkyl, or a linear C1-C6 acyl radical.

In a particular embodiment a second preferred variant of the invention, among the compounds of formula (I), or an optical isomer, stereoisomer and/or diastereoisomer thereof, the compounds for which R1=R3=R5=hydrogen, i.e. the compounds corresponding to formula (III) below, will be chosen:

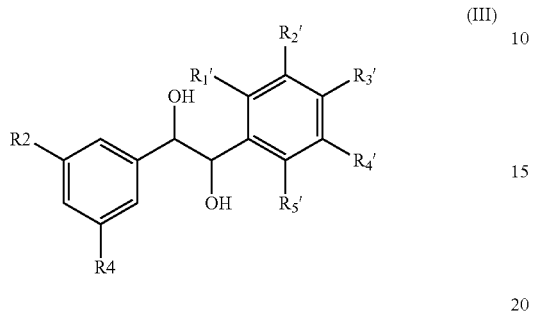

in which:

R2 and R4 independently denote a radical —OR $R_1'$, $R_2'$, $R_4'$ and $R_5'$ independently denote a hydrogen atom or a radical —OR $R_3'$ denotes a radical —OR, R denotes a hydrogen atom, a linear C1-C6 alkyl, a branched C3-C6 alkyl, or a linear C1-C6 acyl radical.

In a particularly preferred manner, among the compounds of formula (III), or an optical isomer, stereoisomer and/or diastereoisomer and/or salts thereof, the compounds that will preferably be chosen are those of formula (III) for which R2=R4=OH, i.e. the compounds of formula (IV) below:

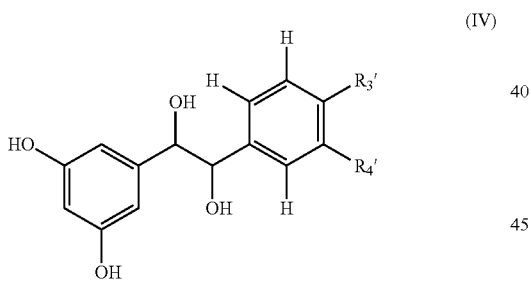

in which $R_3'$ and $R_4'$ independently denote a hydrogen atom or a radical —OR in which R denotes a hydrogen atom or a linear C1-C4 alkyl radical, and preferably in which R denotes a hydrogen atom or a methyl radical.

Preferably the compounds of formula (IV) above are those in which;

$R_4'$ denotes a hydrogen atom or a radical —OR, $R_3'$ denotes a radical —OR, in which R denotes a hydrogen atom or a linear C1-C4 alkyl radical, and preferably in which R denotes a hydrogen atom or a methyl radical.

Among the compounds of formula (III), compounds 4 to 10 below, the optical isomers, stereoisomers and diastereoisomers thereof and/or geometrical isomers thereof and/or salts thereof will be chosen even more particularly:

| Compound | Structure |
|---|---|
| 4 | 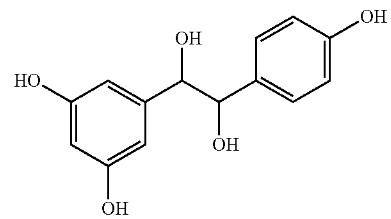 [SMILES: Oc1ccc(C(O)C(O)c2cc(O)cc(O)c2)cc1] |
| 5 | 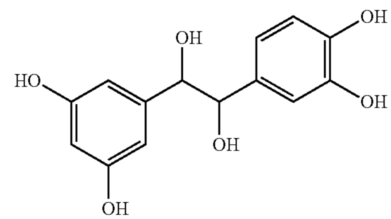 [SMILES: Oc1cc(O)cc(C(O)C(O)c2ccc(O)c(O)c2)c1] |
| 6 | 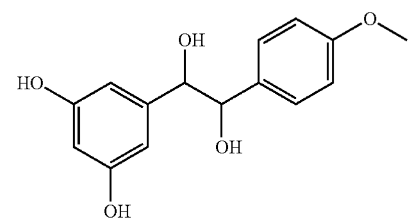 [SMILES: COc1ccc(C(O)C(O)c2cc(O)cc(O)c2)cc1] |
| 7 | 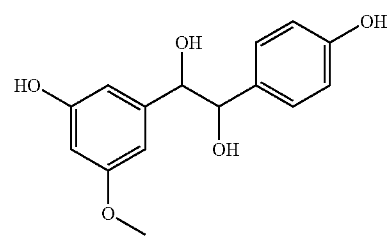 [SMILES: COc1cc(O)cc(C(O)C(O)c2ccc(O)cc2)c1] |
| 8 | 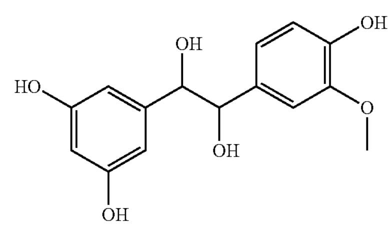 [SMILES: COc1cc(C(O)C(O)c2cc(O)cc(O)c2)ccc1O] |
| 9 | 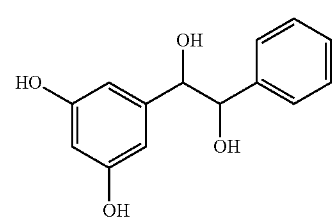 [SMILES: Oc1cc(O)cc(C(O)C(O)c2ccccc2)c1] |
| 10 | 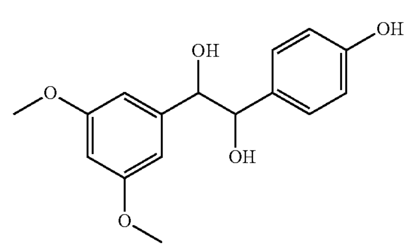 [SMILES: COc1cc(OC)cc(C(O)C(O)c2ccc(O)cc2)c1] |

A subject of the invention is also the novel compounds corresponding to formula (IIIA):

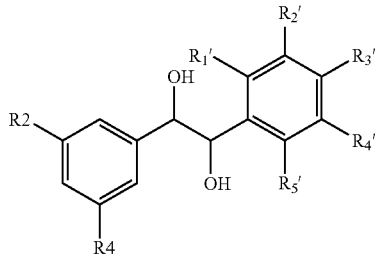

(IIIA)

in which:

R2 and R4 independently denote a radical —OR $R_1'$, $R_2'$, $R_3'$, $R_4'$ and $R_5'$ independently denote a hydrogen atom or a radical —OR R denotes a hydrogen atom or a linear C1-C6 or branched C3-C6 alkyl or linear C2-C6 acyl radical, with the exception of the following 3 compounds:

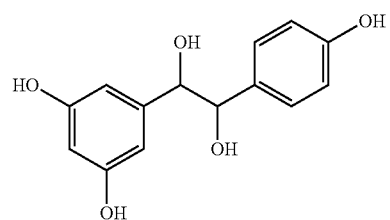 [SMILES: Oc1ccc(C(O)C(O)c2cc(O)cc(O)c2)cc1]

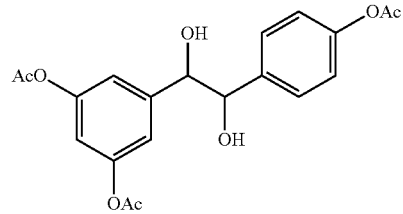

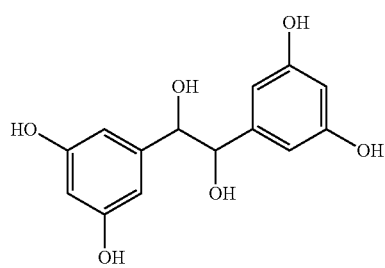

A subject of the invention is also the novel compounds corresponding to formula (IIIA):

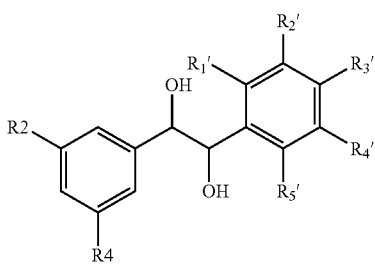

(IIIA)

in which:

R2 and R4 independently denote a radical —OR $R_1'$, $R_2'$, $R_4'$ and $R_5'$ independently denote a hydrogen atom or a radical —OR, $R_3'$ denotes a radical —OR, R denotes a hydrogen atom or a linear C1-C6 or branched C3-C6 alkyl or linear C2-C6 acyl radical, with the exception of the following 3 compounds:

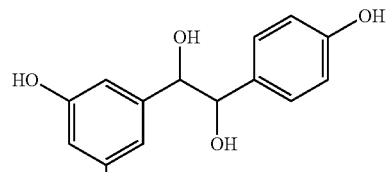

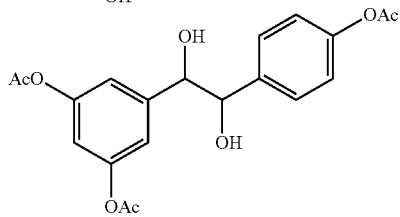

Among the novel compounds of formula (IIIA), mention may be made of the compounds of formula (IIIA) for which R2=R4=OH, i.e. the compounds of formula (IVA) below:

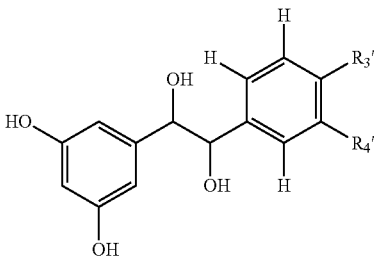

(IVA)

in which $R_3'$ and $R_4'$ independently denote a hydrogen atom or a radical —OR in which R denotes a hydrogen atom or a linear C1-C4 alkyl radical, R preferably denoting a hydrogen atom or a methyl radical with the exception of the following compound:

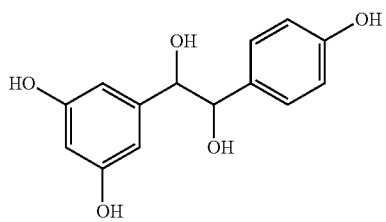 [SMILES: Oc1ccc(C(O)C(O)c2cc(O)cc(O)c2)cc1]

Among the novel compounds of formula (IIIA), mention may be made of the compounds of formula (IIIA) for which R2=R4=OH, i.e. the compounds of formula (IVA) below:

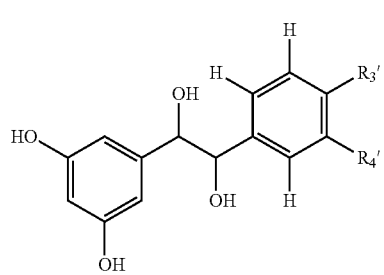

(IVA)

in which $R_4'$ independently denotes a hydrogen atom or a radical —OR in which R denotes a hydrogen atom or a linear C1-C4 alkyl radical, R preferably denoting a hydrogen atom or a methyl radical, and $R_3'$ denotes a radical —OR in which R denotes a hydrogen atom or a linear C1-C4 alkyl radical, R preferably denoting a hydrogen atom or a methyl radical, with the exception of the following compound:

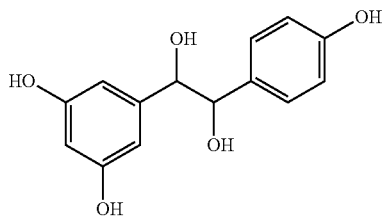

Among the compounds of formula (IIIA), the novel compounds 5 to 10 below, optical isomers, stereoisomers and diastereoisomers and/or geometrical isomer and/or salts will be chosen even more particularly:

Among the compounds of formula (IIIA), the novel compounds 5 to 10 below, optical isomers, stereoisomers and diastereoisomers and/or geometrical isomers and/or salts will be chosen even more particularly:

| Compound | Structure |
|---|---|
| 6 | (structure: 1-(3,5-dihydroxyphenyl)-2-(4-methoxyphenyl)ethane-1,2-diol) |
| 7 | (structure: 1-(4-hydroxyphenyl)-2-(3-hydroxy-5-methoxyphenyl)ethane-1,2-diol) |
| 8 | (structure: 1-(3,5-dihydroxyphenyl)-2-(4-hydroxy-3-methoxyphenyl)ethane-1,2-diol) |
| 10 | (structure: 1-(3,5-dimethoxyphenyl)-2-(4-hydroxyphenyl)ethane-1,2-diol) |

Salts of compounds of formula (I), in particular compounds (II) (III) (IIIA) and/or (IV), may be organic salts and/or minerals. They may be chosen from metal salts, for example aluminum (Al3+), zinc (Zn2+), manganese (Mn2+) or copper (Cu2+); alkali metal salts, for example lithium (Li+), sodium (Na+) or potassium (K+); and alkaline earth metal salts, for example calcium (Ca2+) or magnesium (Mg2+). It may also include salts of formula NH4+ or organic salts of formula NHX3+, NX3 designating an organic amine, the radicals X being identical or different, two or three X radicals can form in pairs a ring with the nitrogen atom which carries them or NX3 possibly denotes an aromatic amine. Organic amines denote in particular alkylamines, such as methylamine, dimethylamine, trimethylamine, triethylamine or ethylamine; hydroxyalkylamines such as 2-hydroxyethylamine, bis-(2-hydroxyethyl) amine or tri-(2-hydroxyethyl) amine; cycloalkylamines such as bicyclohexylamine or glucamine, piperidine; pyridines and the like, for example collidine, quinine or quinoline; and amino acids with basic character, as for example the lysine or arginine.

Preferably salts compounds of formula (I), in particular compounds (II) (III) (IIIA) and/or (IV), are calcium salts.

The compounds corresponding to formula (I) may be prepared in 3 steps from the corresponding compounds (A):

protection of the free phenol functions according to the standard methods known to those skilled in the art (see, for example, *Greene's Protective Groups in Organic Synthesis*, P. G. M. Wutz, T. Greene, ed. Wiley-Blackwell), for example by using the acetate group or the benzyl group as protecting group;

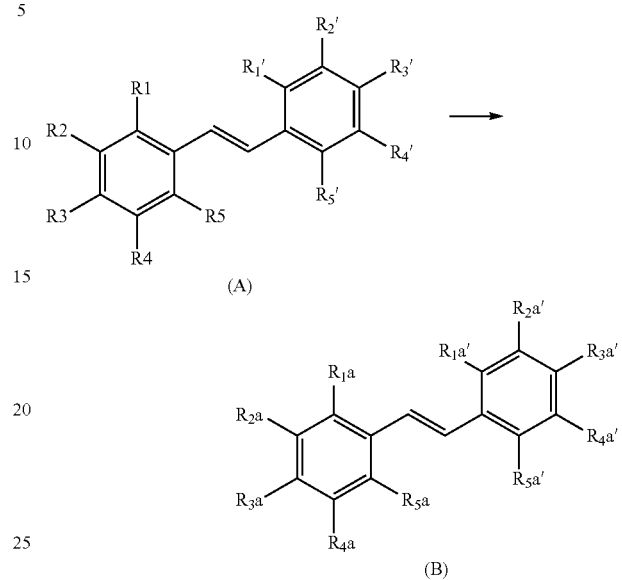

R1 to R5 and $R_1'$ to $R_5'$ having the meanings described previously.

When at least one from among R1 to R5 and $R_1'$ to $R_5'$ denotes a hydroxyl radical OH, the corresponding radical $R_1a$ to $R_5a$ and/or $R_1a'$ to $R_5a'$ denotes O-Prot with Prot denoting a hydroxyl-function protecting group, in particular —CO—CH$_3$ or —CH$_2$-Ph.

When at least one of the substituents R1 to R5 and/or $R_1'$ to $R_5'$ does not denote OH, the corresponding radical $R_1a$ to $R_5a$ and/or $R_1a'$ to $R_5a'$ denotes R1 to R5 and/or $R_1'$ to $R_5'$.

dihydroxylation of the corresponding protected intermediates (B):

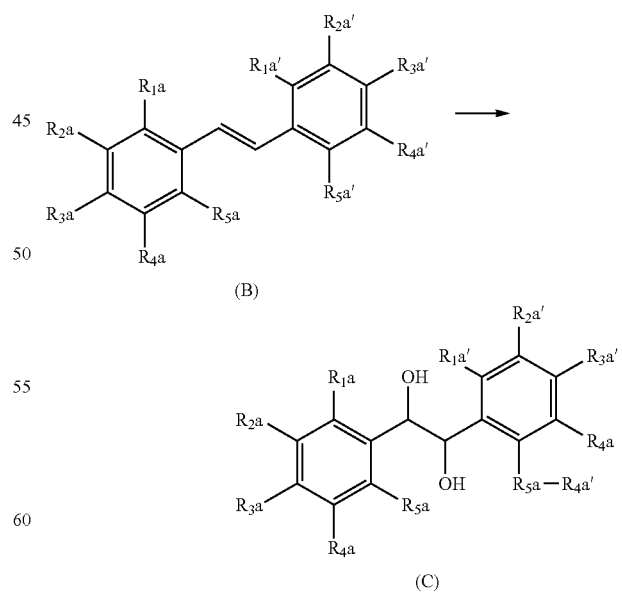

R1 to R5, $R_1'$ to $R_5'$, $R_1a$ to $R_5a$ and $R_1a'$ to $R_5a'$ having the meanings described previously.

The reaction may be performed using the commercial Sharpless systems AD-mix-α (available from the supplier Sigma USA under the reference 392758) or AD-mix-β (available from the supplier Sigma USA under the reference 392766).

The oxidizing system AD-mix (in an amount such that 0.004 eq. of the potassium osmate precatalyst is introduced) is dissolved in an alkanol/water two-phase mixture such as the t-BuOH/water mixture in 1/1 proportions and the medium is stirred at room temperature until dissolution is complete. The following are then successively added:

methanesulfonamide (2 eq.)

intermediate derived from the first step (i.e. protected intermediate (B)) (1 eq.)

an aprotic solvent such as dichloromethane

The reaction medium is maintained at 0-70° C. for 2-96 hours. After cooling to room temperature, it is stirred in contact with sodium sulfite to neutralize the peroxides. The product is extracted with an organic solvent and the organic phases are combined, dried and concentrated. The residue is generally purified by column chromatography on silica gel.

deprotection of the phenol functions, protected beforehand, according to the standard methods known to those skilled in the art (see, for example, *Greene's Protective Groups in Organic Synthesis*, P. G. M. Wutz, T. Greene, ed. Wiley-Blackwell)

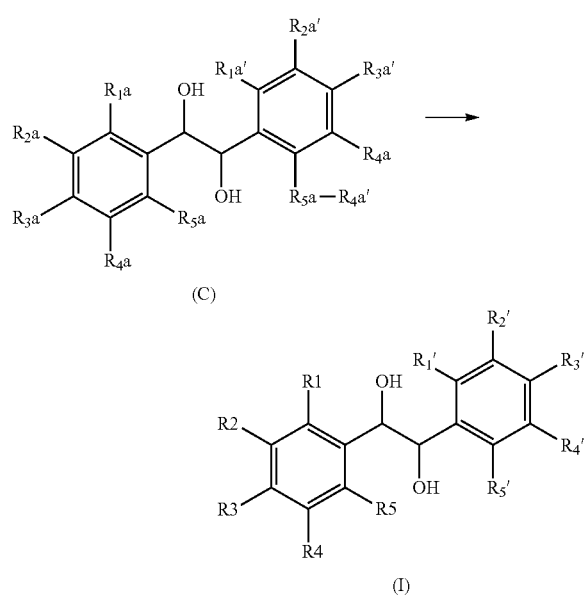

R1 to R5, $R_1'$ to $R_5'$, $R_1a$ to $R_5a$ and $R_1a'$ to $R_5a'$ having the meanings described previously.

When the corresponding compounds (A) are not commercial, they may be obtained via the following metathesis reaction:

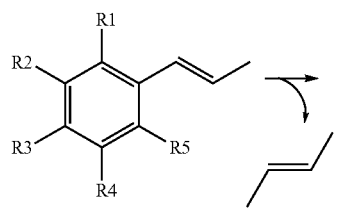

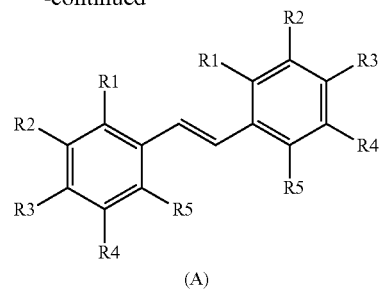

(A)

This reaction may be catalyzed by a commercially available ruthenium complex, such as the Grubbs I, Grubbs II, Hoveyda-Grubbs, Zhan B or Zhan 1C complexes.

Thus, for example, the ruthenium complex (0.0005 eq.-0.20 eq.) is added to a solution of the styrene derivative (1 eq.) in an anhydrous aprotic solvent such as anhydrous dichloromethane or anhydrous toluene. The reaction mixture is refluxed (50-150° C.) under an inert atmosphere for 0.5-24 hours. After cooling to room temperature, the solvent is evaporated off under reduced pressure and the residue is purified to isolate the expected intermediate (A), either by recrystallization from a polar aprotic solvent such as acetonitrile, or by column chromatography on silica gel.

According to these routes, the compounds of formulae (I), (II), (III) and (IV) and in particular the novel compounds of formulae (IIIA) and (IVA), in particular compounds 5 to 10 described previously, are obtained.

The present invention also relates to a composition, especially a cosmetic composition, comprising, in a physiologically acceptable medium, at least one compound of formula (I).

In particular, the composition is suitable for topical application to the skin, in particular the skin of human individuals.

The present invention also relates to a composition, especially a cosmetic composition, comprising, in a physiologically acceptable medium, at least one novel compound of formula (IIIA) and preferably at least one compound chosen from compounds 5 to 10 described previously.

The present invention also relates to a composition, especially a cosmetic composition, comprising, in a physiologically acceptable medium, at least one novel compound of formula (IIIA) and preferably at least one compound chosen among the compounds 5, 6, 7, 8, and/or 10 described previously.

The compound of formulae (I) or (IIIA) may be present, alone or as a mixture, in the compositions according to the invention in an amount of between 0.01% and 30% by weight, preferably between 0.1 and 10% by weight, especially between 0.5% and 5% by weight, relative to the total weight of the composition.

The compositions according to the invention also comprise a physiologically acceptable medium, which will preferentially be a cosmetically acceptable medium, i.e. a medium that has no unpleasant odor, color or appearance, and that does not cause the user any unacceptable stinging, tautness or redness. For the purposes of the present invention, the term "physiologically acceptable medium" means a medium that is compatible with human keratin materials such as the skin of the body or of the face, the lips, mucous membranes, the eyelashes or the nails.

The compositions according to the invention may comprise any cosmetic ingredient usually used in the field of application envisioned.

Thus, a composition according to the invention may comprise at least one cosmetic ingredient chosen from water; organic solvents, in particular $C_1$-$C_6$ alcohols and $C_2$-$C_{10}$ carboxylic acid esters; hydrocarbon-based oils, silicone oils, fluoro oils, waxes, pigments, fillers, dyes, surfactants, emulsifiers, cosmetic active agents, UV-screening agents, film-forming polymers, hydrophilic or lipophilic gelling agents, hydrophilic or lipophilic thickeners, preserving agents, fragrances, odor absorbers/neutralizers and antioxidants.

These optional ingredients may be present in the composition in a proportion of from 0.001% to 99% by weight and especially from 0.1% to 40% by weight relative to the total weight of the composition.

The compositions according to the invention may be compositions that may comprise a fatty phase and/or an aqueous phase.

Depending on their nature, these optional ingredients may be introduced into the fatty phase or into the aqueous phase of the composition, or into lipid vesicles. In any case, these ingredients, and the proportions thereof, will be chosen by a person skilled in the art such that the advantageous properties of the compounds according to the invention are not, or are not substantially, adversely affected by the envisaged addition.

As oils that may be used in the invention, mention may be made of mineral oils, hydrocarbon-based oils such as liquid petroleum jelly, oils of plant origin, oils of animal origin, synthetic oils and silicone-based oils. When it is present, the fatty phase may also contain fatty alcohols, fatty acids or waxes.

As hydrophilic thickeners or gelling agents, mention may be made of carboxyvinyl polymers (carbomer), acrylic copolymers such as acrylate/alkyl acrylate copolymers, polyacrylamides, polysaccharides, natural gums and clays, and, as lipophilic thickeners or gelling agents, mention may be made of modified clays such as bentones, metal salts of fatty acids and hydrophobic silica.

A composition according to the invention may comprise at least one cosmetic active agent other than the compounds of formula (I), in particular at least one compound chosen from: desquamating agents; moisturizers; depigmenting or propigmenting agents; anti-glycation agents; NO-synthase inhibitors; agents for stimulating the synthesis of dermal or epidermal macromolecules and/or for preventing their degradation; agents for stimulating fibroblast and/or keratinocyte proliferation or for stimulating keratinocyte differentiation; dermo-decontracting agents; tensioning agents; agents acting on the capillary circulation; agents acting on the energy metabolism of cells; and mixtures thereof. This composition may be in any galenical form normally used in the cosmetic or dermatological field, and especially in the form of an optionally gelled aqueous or aqueous-alcoholic solution, a dispersion, optionally a two-phase dispersion, of the lotion type, an emulsion obtained by dispersion of a fatty phase in an aqueous phase (O/W) or vice versa (W/O), or a triple (W/O/W or O/W/O) emulsion or a vesicular dispersion of ionic and/or nonionic type; aqueous or oily gels. These compositions are prepared according to the usual methods.

The composition may be more or less fluid and may have the appearance of a white or colored cream, an ointment, a milk, a lotion, a serum, a paste, a gel or a mousse. It may optionally be applied in the form of an aerosol. It may also be in solid form, in particular in stick form.

When the composition is an emulsion, the proportion of the fatty phase may range from 5% to 80% by weight and preferably from 8% to 50% by weight relative to the total weight of the composition. The emulsifiers may be present in a proportion ranging from 0.3% to 30% by weight and preferably from 0.5% to 20% by weight, relative to the total weight of the composition.

The composition according to the invention may constitute a skincare composition, in particular a cleansing, protection, treatment, or care cream for the face, for the hands, for the feet, for the major anatomical folds or for the body (for example, day creams, night creams, makeup-removing creams, foundation creams, antisun creams); a makeup-removing milk, a protective or care body milk or, an antisun milk; or a lotion, a gel or foam for skincare, such as a cleansing lotion.

A composition according to the invention is advantageously an anti-aging composition, especially a care composition for treating and/or combating, especially cosmetically, the external signs of aging of the skin.

The composition is more particularly a composition for caring for mature skin.

The composition may also be a makeup composition, especially a foundation.

In the description and in the examples that follow, unless otherwise mentioned, the percentages are weight percentages and the ranges of values written in the form "between . . . and . . . " include the stated lower and upper limits. The ingredients are mixed, before being formed, in the order and under conditions that may be readily determined by those skilled in the art.

The examples below are presented as nonlimiting illustrations of the field of the invention.

EXAMPLE 1

Preparation of Compound 1

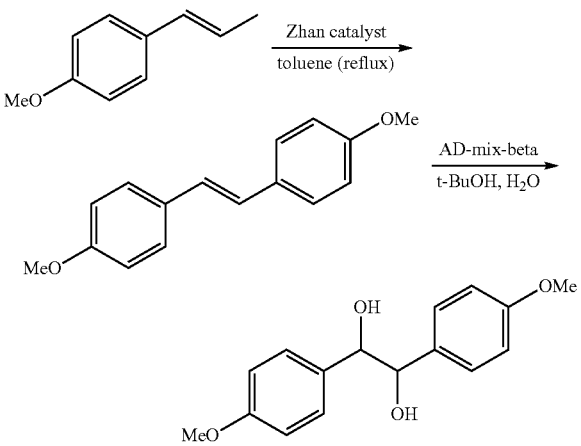

1st Step

The Zhan catalyst (commercially available from the supplier Sigma USA under the reference 762261) (44 mg, 0.061 mmol, 0.01 eq.) is added to a solution of commercial anethole (298 mg, 2.0 mmol) in anhydrous toluene. The reaction mixture is heated at 110° C. under an inert atmosphere ($N_2$) for 2 hours. After cooling to room temperature, the toluene is evaporated off under reduced pressure and the residue is purified by column chromatography on silica gel (5/1 hexane/dichloromethane) to isolate the intermediate in the form of a white solid after evaporating off the solvents (433 mg, 90% yield).

The $^1$H NMR spectra and mass spectra are in accordance with the expected structure.

2nd Step

The intermediate derived from the first step and AD-mix-β (1.9 g) are dissolved in 8 mL of a t-BuOH/water two-phase mixture (1/1 proportions) and the medium is stirred at room temperature for 16 hours.

The product is extracted with ethyl acetate and the organic phase is washed with saturated aqueous $Na_2SO_3$ solution and then with aqueous 2N NaOH solution, dried over sodium sulfate and then concentrated to dryness. The residue is purified by column chromatography on silica gel (EtOAc/hexanes=1/3) to give compound 1 in the form of a white solid (105 mg, 72% yield).

The $^1$H NMR spectra and mass spectra are in accordance with the expected structure.

EXAMPLE 2

Preparation of Compound 3

Compound 3 is obtained in 4 steps according to the sequence described below:

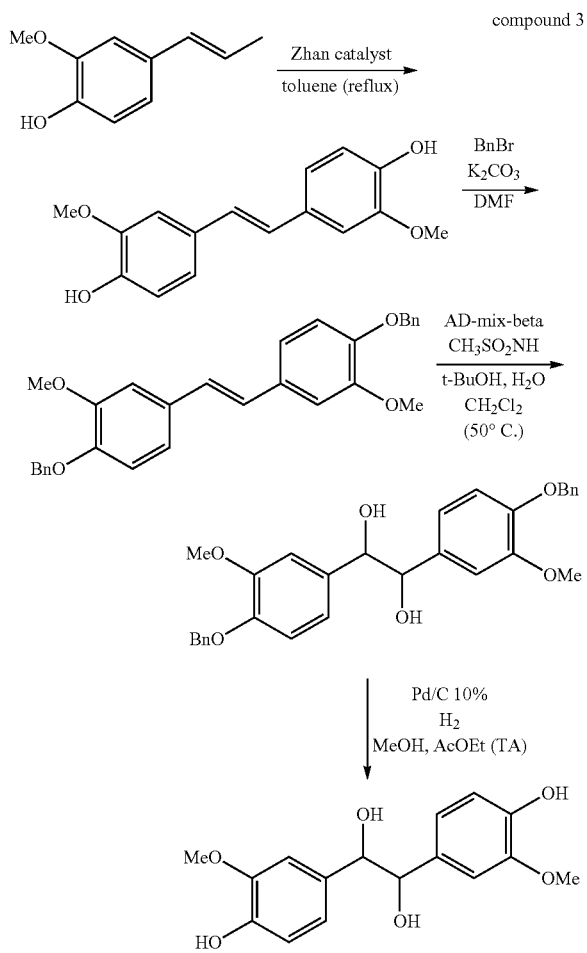

1st Step

The Zhan catalyst (commercially available from the supplier Sigma USA under the reference 762261) (447 mg, 0.061 mmol, 0.01 eq.) is added to a solution of commercial isoeugenol (10 g, 61 mmol, 1 eq.) in anhydrous toluene (50 mL). The reaction mixture is heated at 110° C. under an inert atmosphere for 24 hours. After cooling to room temperature, the toluene is evaporated off under reduced pressure and the residue is recrystallized from acetonitrile to give the expected intermediate in the form of a gray solid (6.0 g, 75% yield).

2nd Step

The intermediate derived from the first step (5.9 g, 21.8 mmol, 1 eq.), dissolved in DMF (100 mL), is treated with benzyl bromide (11.2 g, 65.4 mmol, 3 eq.) in the presence of potassium carbonate (12.0 g, 87.2 mmol, 4 eq.). The reaction mixture is stirred at room temperature for 12 hours and the product is then precipitated by adding a large volume of water (100 mL). After filtration, the solid is washed with water and then with hexane and dried under vacuum. The intermediate is obtained in the form of a pale yellow solid (9.8 g, 95% yield).

3rd Step

AD-mix-β (9 g) is dissolved in 120 mL of a t-BuOH/water two-phase mixture (1/1 proportions) and the medium is stirred at room temperature until dissolution is complete. The following are then successively added:
methanesulfonamide (1.3 g, 13.3 mmol, 2 eq.)
intermediate derived from the second step (3.0 g, 6.6 mmol)
dichloromethane (50 ml)

The reaction medium is maintained at 50° C. for 72 hours. After cooling to room temperature, it is stirred at room temperature in contact with sodium sulfite (10 g) to neutralize the peroxides. The product is extracted 3 times with dichloromethane and the organic phases are combined, dried over sodium sulfate and concentrated to dryness. The residue is purified by column chromatography on silica gel (EtOAc/hexanes=1/2) to give the expected intermediate (protected compound 3), after evaporating off the solvents, in the form of a white solid (1.0 g, 30% yield).

4th Step

The catalyst 10% Pd/C (200 mg) is suspended in a solution of the intermediate derived from the third step in a 1/1 MeOH/EtOAc mixture (40 mL). The reaction medium is stirred at room temperature under an atmosphere of dihydrogen for 24 hours. After removal of the catalyst by filtration, the filtrate is concentrated and the residue is purified by column chromatography on silica gel (dichloromethane/EtOAc: 1/2) to give, after evaporating off the solvents, compound 3 in the form of a white solid (1.0 g, 85% yield).

The $^1$H NMR spectra and mass spectra are in accordance with the expected structure.

EXAMPLE 3

Preparation of Compound 4

Compound 4 is obtained in 3 steps from commercial resveratrol, according to the protection-dihydroxylation-deprotection sequence described below:

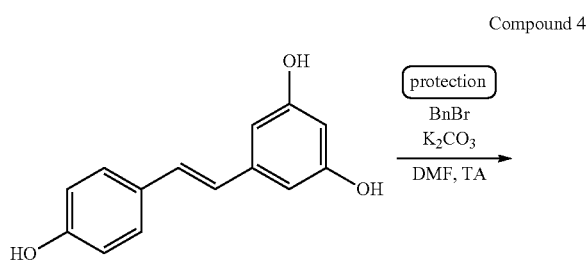

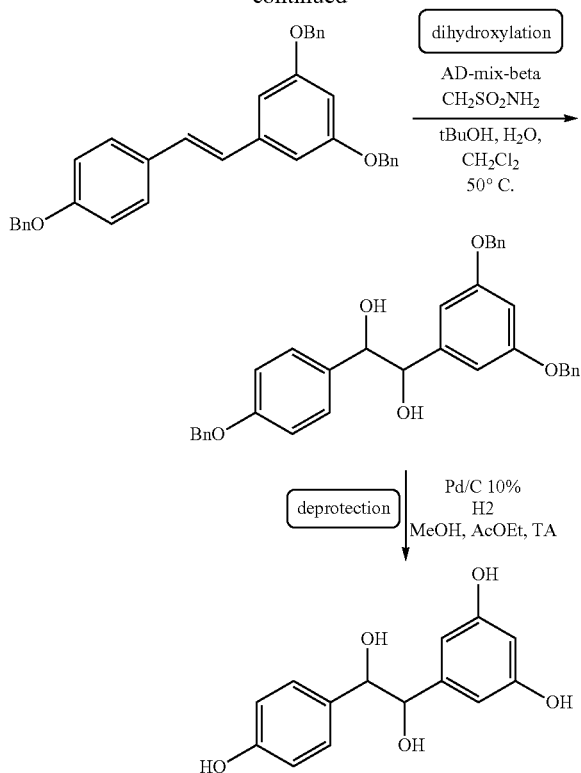

1st Step

The following are placed in a three-necked flask:
- resveratrol (1.0 g, 4.4 mmol)
- N,N-dimethylformamide (15 ml)
- benzyl bromide (3.4 g, 19.7 mmol, 4.5 eq.)
- potassium carbonate (3.6 g, 26.3 mmol, 6 eq.).

The reaction mixture is stirred at room temperature for 16 hours and then poured into 20 mL of water. The solid thus formed is filtered off and washed with water and then with petroleum ether. It is dried under vacuum to give a white powder corresponding to the protected resveratrol (m=2.1 g, 95% yield).

The intermediate thus obtained is used as obtained in the following step.

2nd Step

AD-mix-β (26 g) is dissolved in 200 mL of a t-BuOH/water two-phase mixture (1/1 proportions) and the medium is stirred at room temperature until dissolution is complete. The following are then successively added:
- methanesulfonamide (3.5 g, 37.2 mmol)
- the intermediate derived from the first step (9.3 g, 18.6 mmol)
- dichloromethane (30 ml)

The reaction medium is maintained at 50° C. for 72 hours. After cooling to room temperature, it is stirred at room temperature in contact with sodium sulfite (10 g) to neutralize the peroxides. The product is extracted 3 times with dichloromethane and the organic phases are combined, dried over sodium sulfate and concentrated to dryness. The residue is purified by column chromatography on silica gel (EtOAc/hexanes=1/2) to give the expected intermediate (protected compound 4) in the form of a pale yellow solid after evaporating off the solvents (m=7.4 g, 70% yield).

3rd Step

The following are placed in a round-bottomed flask:
- the intermediate derived from the second step (11 g, 20.7 mmol)
- ethyl acetate (50 mL)
- methanol (50 mL)
- 10% Pd/C (1.1 g)

The reaction medium is stirred at room temperature under an atmosphere of dihydrogen for 8 hours. The catalyst is then removed by filtration and the filtrate is concentrated under reduced pressure. The residue is purified by column chromatography on silica gel (dichloromethane/EtOAc: 1/2) to give compound 4 in the form of a white solid after evaporating off the solvents (m=4.7 g, 87% yield).

The $^1$H NMR spectra and mass spectra are in accordance with the expected structure.

EXAMPLE 4

Normal human epidermal keratinocytes are seeded at 180 000 cells per well and cultured in SFM culture medium (supplier Gibco) supplemented with 0.25 ng/ml EGF, 25 μg/ml of pituitary extract and 25 μg/ml gentamicin, up to confluence, and incubated in a humid oven at 37° C. and 5% CO2. The culture medium was then replaced with test medium (SFM (Gibco) supplemented with 25 μg/ml gentamicin) containing or not containing (control) the test compounds, the combinations or the reference (AICAR—(5-amino-4-imidazolecarboxamide riboside) at 500 μM). The cells were then incubated for 12 hours.

The level of expression of p-AMPK was analyzed by Western blotting.

At the end of the incubation, the proteins were extracted and quantified and then separated by electrophoresis on 10% polyacrylamide gel and then transferred onto a nitrocellulose membrane.

After saturation of the membranes in PBS/Tween/1% BSA solution, the phospho-AMPK proteins (Thr-172) (p-AMPK) and GAPDH were successively revealed using specific antibodies that were themselves revealed using an anti-immunoglobulin-peroxidase conjugate. After washing with PBS/Tween, the peroxidase activity and thus the proteins of interest was revealed via the ECL+ (enhanced chemiluminescence) method. Between each successive revelation, the antibodies were detached using a "stripping" buffer. The images were acquired with a Fuji LAS 3000 chemiluminescence scanner (Fujifilm) and the densitometric analyses were performed using the Multigauge software (Fujifilm).

An increase in the phosphorylated form of AMPK (active form of the enzyme) relative to the control is evaluated in this test.

Results

Expressed in the form of the p-AMPK/GAPDH ratio relative to the control (100%):

| compound | AICAR 500 μM | 1 μM | 10 μM | 100 μM |
|---|---|---|---|---|
| 1 | 290% | 133% | 171% | 198% |
| 2 | 283% | 94% | 134% | 149% |
| 3 | 357% | 112% | 147% | 158% |
| 4 | 290% | 132% | 140% | 159% |

EXAMPLE 5

The following anti-aging composition is prepared:
The percentages are indicated on a weight basis.

| | |
|---|---|
| Compound of Example 3 | 2% |
| Glycerol | 12% |
| Polyacrylamide at 40% AM (Sepigel 305 from SEPPIC) | 1% AM |
| Mixture of polydimethylsiloxane containing α,ω-hydroxyl and cyclopentadimethylsiloxane groups (15/85) | 2% |
| Preserving agents | qs |
| Fragrance | qs |
| Water | qs 100% |

AM: active material
When applied to the skin, this cream reduces the signs of aging of the skin.

The invention claimed is:

1. A process for preventing and/or reducing the signs of aging of the skin which comprises applying to the skin one or more compounds of formula (I):

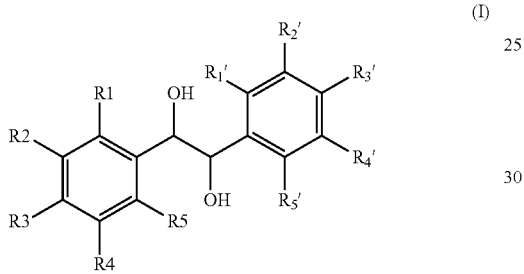

(I)

in which R1, $R_1'$, R2, $R_2'$, R3, R4, $R_4'$, R5 and $R_5'$ independently denote a hydrogen atom or a radical —OR, and
$R_3'$ denotes a radical —OR,
R independently denotes a hydrogen atom, a linear C1-C6 alkyl, a branched C3-C6 alkyl, or a linear C1-C6 acyl radical,
an optical isomer, stereoisomer, diastereoisomer, geometrical isomer, and/or salt thereof.

2. The process as claimed in claim 1, wherein, in the one or more compounds of formula (I), R1, $R_1'$, R5 and $R_5'$ denote a hydrogen atom,
R2, $R_2'$, R3, R4 and $R_4'$ independently denote a hydrogen atom or a radical —OT1 in which T1 denotes a hydrogen atom or a linear C1-C4 alkyl radical, and
$R_3'$ denotes a radical —OT1 in which T1 denotes a hydrogen atom or a linear C1-C4 alkyl radical.

3. The process as claimed in claim 1, wherein the one or more compounds of formula (I) is a compound of formula (II):

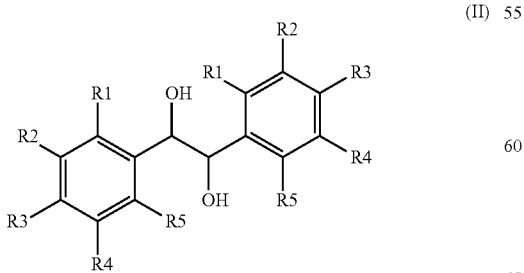

(II)

in which R1, R2, R4 and R5 independently denote a hydrogen atom or a radical —OR, R denotes a hydrogen atom, a linear C1-C6 alkyl, a branched C3-C6 alkyl or a linear C1-C6 acyl radical, and
R3 denotes a radical —OR, R denotes a hydrogen atom, a linear C1-C6 alkyl, a branched C3-C6 alkyl, or a linear C1-C6 acyl radical.

4. The process as claimed in claim 3, in which R1 and R5 denote a hydrogen atom,
R2 and R4 independently denote a hydrogen atom or a radical —OT2 with T2 denoting a hydrogen atom or a linear C1-C4 alkyl radical, and
R3 denotes a radical —OT2 with T2 denoting a hydrogen atom or a linear C1-C4 alkyl radical.

5. The process as claimed in claim 1, wherein the one or more compounds is chosen from compounds 1 to 3 below, an optical isomer, stereoisomer, diastereoisomer and/or salts thereof:

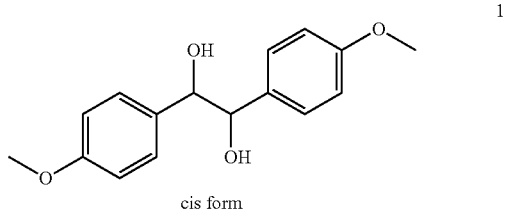

1 cis form

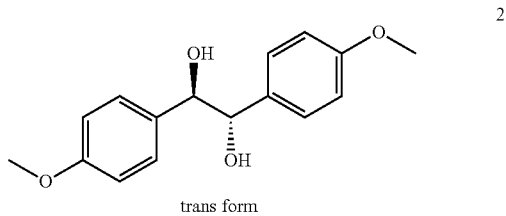

2 trans form

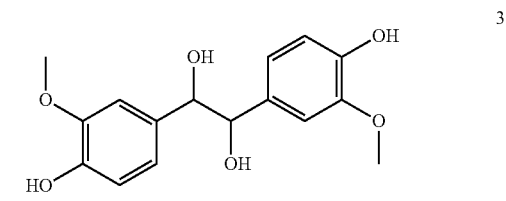

3

6. The process as claimed in claim 1, wherein the one or more compounds of formula (I) is a compound of formula (III):

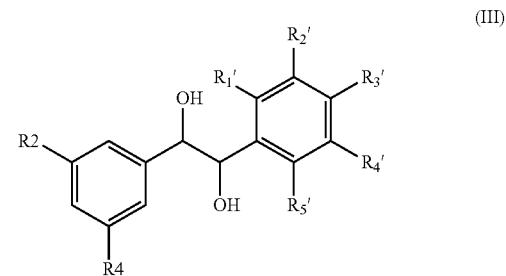

(III)

in which:
R2 and R4 independently denote —OR
$R_1'$, R2, $R_2'$, $R_4'$, and $R_5'$ independently denote a hydrogen atom or a radical —OR,
$R_3'$ denotes a radical —OR,
R denotes a hydrogen atom, a linear C1-C6 alkyl, a branched C3-C6 alkyl, or a linear C1-C6 acyl radical.

7. The process as claimed in claim 1, wherein the one or more compounds of formula (I) is chosen from compounds 4 to 10 below, an optical isomer, stereoisomer, diastereoisomer, geometrical isomer, and/or salt thereof:

| Compound | Structure |
|---|---|
| 4 | 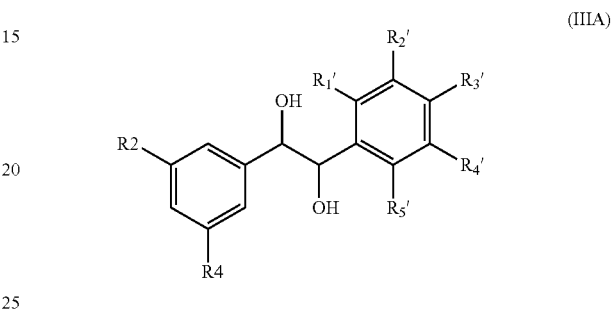 |
| 5 | 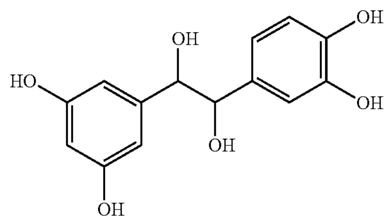 [SMILES: Oc1cc(O)cc(C(O)C(O)c2ccc(O)c(O)c2)c1] |
| 6 | 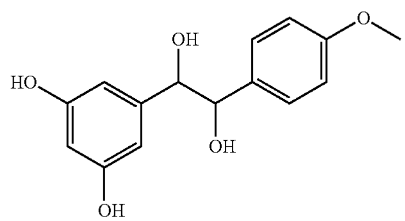 [SMILES: COc1ccc(C(O)C(O)c2cc(O)cc(O)c2)cc1] |
| 7 | 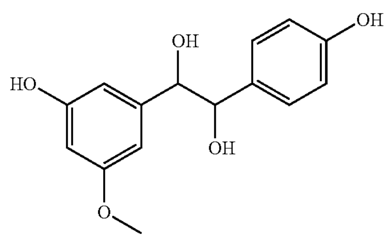 [SMILES: COc1cc(O)cc(C(O)C(O)c2ccc(O)cc2)c1] |
| 8 | 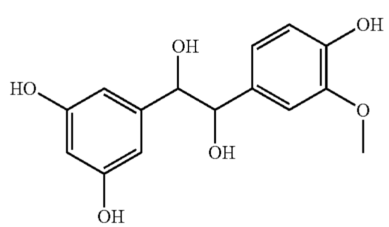 [SMILES: COc1cc(C(O)C(O)c2cc(O)cc(O)c2)ccc1O] |
| 10 | 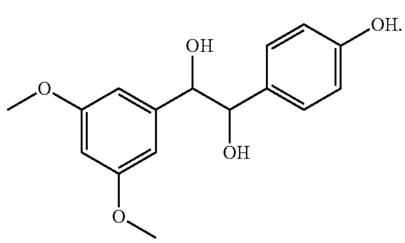 [SMILES: COc1cc(OC)cc(C(O)C(O)c2ccc(O)cc2)c1] |

8. The process as claimed in claim 1, wherein the one or more compounds of formula (I) is present, in a composition containing a physiologically acceptable medium, at a concentration of between 0.0001% and 40% relative to the total weight of the composition.

9. The process according to claim 1, which is a cosmetic treatment process for reducing or preventing the signs of aging of mature and/or wrinkled skin, comprising applying the one or more compounds of formula (I) or a composition containing the one or more compounds of formula (I) to the mature and/or wrinkled skin.

10. The cosmetic treatment process as claimed in claim 9, which is intended for promoting the renewal of the keratinocytes and for reducing or preventing signs chosen from thinning of the epidermis, surface wrinkles and impairment of the barrier function.

11. A compound of formula (IIIA):

(IIIA)

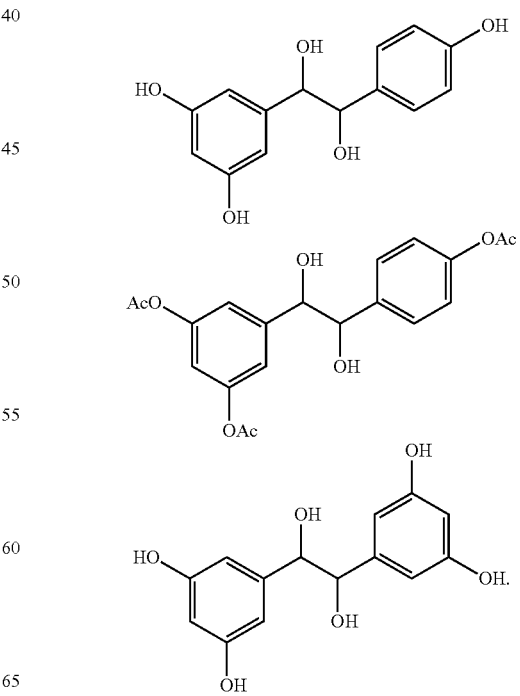

in which:
R2 and R4 independently denote a radical —OR
$R_1'$, $R_2'$, $R_4'$ and $R_5'$ independently denote a hydrogen atom or a radical —OR,
$R_3'$ denotes a radical —OR,
R independently denotes a hydrogen atom, a linear C1-C6 alkyl, a branched C3-C6 alkyl, or a linear C2-C6 acyl radical, an optical isomer, stereoisomer, diastereoisomers, geometrical isomer and/or salt thereof, and provided that the radical —OR for at least one of R2 and R4 is other than —O linear C1-C6 alkyl, and
with the exception of the following 3 compounds:

12. The compound as claimed in claim 11, wherein the compound of formula (IIIA) is a compound of formula (IVA):

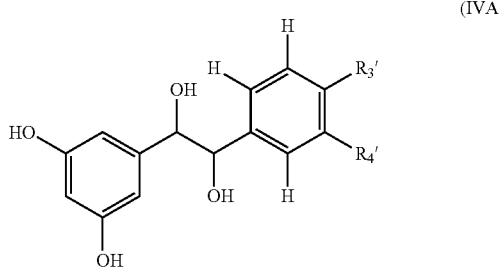
(IVA)

in which $R_4'$ denotes a hydrogen atom or a radical —OR in which R denotes a hydrogen atom or a linear C1-C4 alkyl radical, and
$R_3'$ denotes a radical —OR in which R denotes a hydrogen atom or a linear C1-C4 alkyl radical,
with the exception of the following compound:

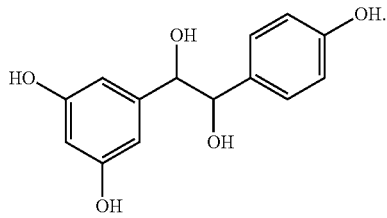 [SMILES: Oc1ccc(C(O)C(O)c2cc(O)cc(O)c2)cc1]

13. The compound as claimed in claim 11, wherein the compound of formula (IIIA) is chosen from compounds 5 to 8 below:

| Compound | Structure |
|---|---|
| 5 | 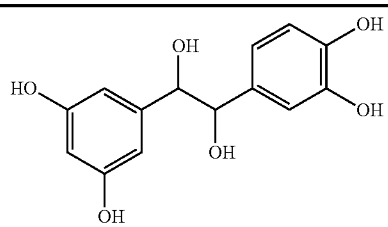 |
| 6 | 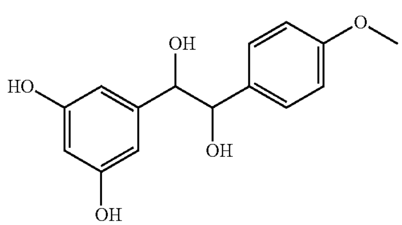 [SMILES: COc1ccc(C(O)C(O)c2cc(O)cc(O)c2)cc1] |
| 7 | 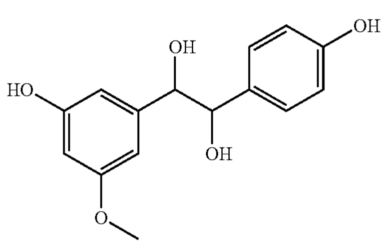 [SMILES: COc1cc(O)cc(C(O)C(O)c2ccc(O)cc2)c1] |
| 8 | |

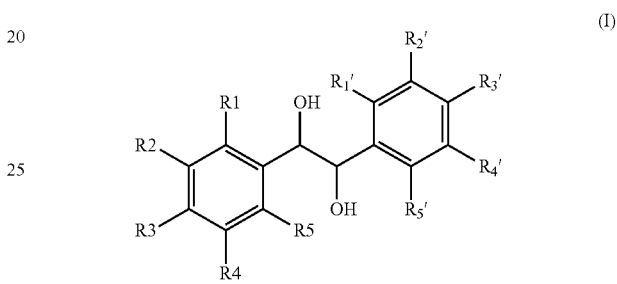

14. A cosmetic composition in the form of a gel or a mousse comprising, in a physiologically acceptable medium, at least one compound of formula (I)

(I)

in which R1, $R_1'$, R2, $R_2'$, R3, R4, $R_4'$, R5 and $R_5'$ independently denote a hydrogen atom or a radical —OR, and
$R_3'$ denotes a radical —OR,
R denotes a hydrogen atom, a linear C1-C6 alkyl, a branched C3-C6 alkyl, or a linear C1-C6 acyl radical, an optical isomer, stereoisomer, diastereoisomer, geometrical isomer and/or salt thereof.

15. The composition as claimed in claim 14, in which the at least one compound of formula (I) is present, alone or as a mixture, in an amount of between 0.01% and 30% by weight relative to the total weight of the composition.

16. The composition as claimed in claim 14, comprising at least one cosmetic ingredient chosen from water; organic solvents; hydrocarbon-based oils, silicone oils, fluoro oils, waxes, pigments, fillers, dyes, surfactants, emulsifiers, cosmetic or dermatological active agents, UV-screening agents, film-forming polymers, hydrophilic or lipophilic gelling agents, hydrophilic or lipophilic thickeners, preserving agents, fragrances, odor absorbers and antioxidants.

17. The composition as claimed in claim 14, in which the physiologically acceptable medium further comprises at least one cosmetic active agent selected from the group consisting of desquamating agents; moisturizers; depigmenting agents; propigmenting agents; anti-glycation agents; NO-synthase inhibitors; agents for stimulating the synthesis of dermal macromolecules; agents for stimulating the synthesis of epidermal macromolecules; agents for preventing the degradation of dermal macromolecules; agents for preventing the degradation of epidermal macromolecules; agents for stimulating fibroblast proliferation; agents for keratinocyte proliferation; agents for stimulating keratinocyte differentiation; dermo-decontracting agents; tensioning agents; agents acting on microcirculation; agents acting on the energy metabolism of cells; and mixtures thereof.

18. A composition comprising, in a physiologically acceptable medium, at least one compound of formula (IIIA) as claimed in claim 11.

19. A non-therapeutic cosmetic process for treating the skin, comprising applying to the skin a cosmetic composition as defined in claim 14.

20. The process as claimed in claim 19, comprising applying the composition to mature and/or wrinkled skin.

21. A cosmetic composition in the form of a cream, an ointment, a milk, a lotion, a serum, a paste, a gel or a mousse comprising, in a physiologically acceptable medium, at least one compound of formula (I)

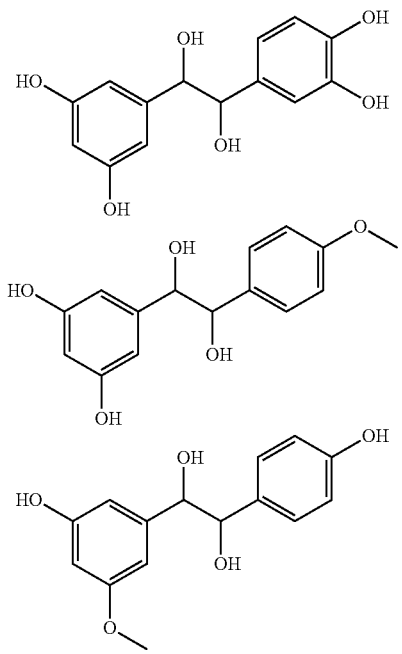

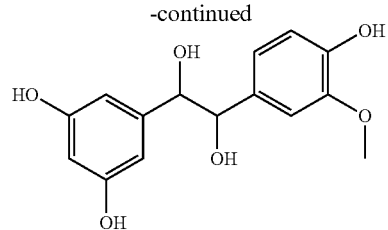

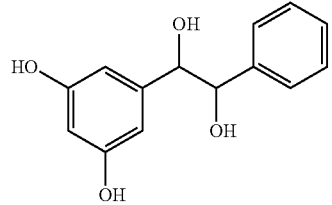

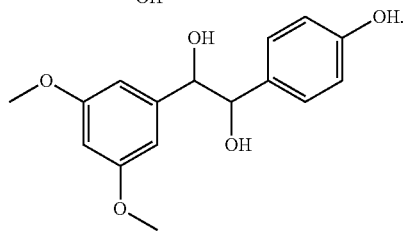

in which, $R_1'$, R2, $R_2'$, R4, $R_4'$, and $R_5'$ independently denote a hydrogen atom or a radical —OR, R1, R3 and R5 each denotes a hydrogen atom and $R_3'$ denotes a radical —OR, R denotes a hydrogen atom, a linear C1-C6 alkyl, a branched C3-C6 alkyl, or a linear C1-C6 acyl radical, an optical isomer, stereoisomer, diastereoisomer, geometrical isomer and/or salt thereof.

* * * * *